(12) United States Patent
Kurtev (10) Patent No.: US 10,449,352 B2
(45) Date of Patent: Oct. 22, 2019

(54) GUIDING TUBE FOR STIMULATION LEADS

(71) Applicant: Brainlab AG, Munich (DE)

(72) Inventor: Dimitar Kurtev, Feldkirchen (DE)

(73) Assignee: BRAINLAB AG, Munich (DE)

( * ) Notice: Subject to any disclaimer, the term of this patent is extended or adjusted under 35 U.S.C. 154(b) by 244 days.

(21) Appl. No.: 15/431,564

(22) Filed: Feb. 13, 2017

(65) Prior Publication Data

US 2017/0291024 A1 Oct. 12, 2017

(30) Foreign Application Priority Data

Dec. 15, 2015 (WO) .................. PCT/EP2015/079759

(51) Int. Cl.
| | | |
|---|---|---|
| *A61N 1/05* | (2006.01) | |
| *A61M 25/06* | (2006.01) | |
| *A61N 1/08* | (2006.01) | |
| *A61B 17/34* | (2006.01) | |
| *A61B 34/20* | (2016.01) | |

(52) U.S. Cl.
CPC ....... *A61N 1/0534* (2013.01); *A61M 25/0662* (2013.01); *A61N 1/08* (2013.01); *A61B 17/3468* (2013.01); *A61B 2034/2051* (2016.02); *A61B 2034/2055* (2016.02); *A61M 2210/0693* (2013.01)

(58) Field of Classification Search
CPC ................... A61N 1/05; A61N 1/0534; A61N 2001/0578; A61B 2019/208
See application file for complete search history.

(56) References Cited

U.S. PATENT DOCUMENTS

| | | | |
|---|---|---|---|
| 2008/0269740 A1 | 10/2008 | Bonde et al. | |
| 2009/0157136 A1 | 6/2009 | Yang et al. | |
| 2009/0204192 A1* | 8/2009 | Carlton | A61N 1/0529 607/116 |
| 2014/0275991 A1 | 9/2014 | Potter et al. | |
| 2015/0180161 A1* | 6/2015 | Olson | H01R 13/5224 439/587 |

FOREIGN PATENT DOCUMENTS

| | | |
|---|---|---|
| WO | WO2008082802 A2 | 7/2008 |
| WO | WO2009102508 A1 | 8/2009 |
| WO | WO2009152486 A1 | 12/2009 |

OTHER PUBLICATIONS

Extended European Search Report for European Patent Application No. 17000248.9 dated Jun. 20, 2017.

* cited by examiner

*Primary Examiner* — Vi X Nguyen
(74) *Attorney, Agent, or Firm* — Middleton Reutlinger (57) ABSTRACT

The present invention relates to a guiding tube for stimulation leads, including comprising a longitudinal, dimensionally stable tubular body enclosing an inner channel adapted to receive a stimulation lead, wherein at least one section of an otherwise electrically insulated inner surface of the tubular body has electroconductive properties. The present invention further relates to a corresponding stimulation lead placing system including such guiding tube, and to a corresponding computer program for placing a stimulation lead, utilizing such guiding tube.

8 Claims, 3 Drawing Sheets

GUIDING TUBE FOR STIMULATION LEADS

TECHNICAL FIELD

The present invention relates to a guiding tube for stimulation leads which is utilized during a medical procedure to advance a stimulation lead through tissue to a desired target region.

SUMMARY

Deep brain stimulation (DBS) is a surgical procedure used to treat a variety of disabling neurological symptoms such as tremor, rigidity, stiffness, slow movement and walking problems which may come along with Parkinson's disease (PD). In order to treat those symptoms, so-called neurostimulators are employed which deliver an electrical stimulation via a lead connected to the neurostimulator, to affected target regions within the patient's brain. Positioning guides which are substantially dimensionally stable help in advancing flexible stimulation leads through tissue along a predefined trajectory to the desired target region. After the stimulation lead has been placed at the correct position within the brain, the positioning guide may either be retracted or may even remain in place for a longer period of time while DBS is performed. So-called guiding tubes or insertion cannulas are commonly used types of a positioning guide, which provide a circumferential enclosure for a stimulation lead placed therein for at least the duration of the placing procedure. Since such guiding tubes are stiff and dimensionally stable, the guiding tube can be expected to maintain its original shape while being advanced through tissue. Thus, its overall position can be determined with the help of medical tracking systems that allow image guided surgery. What cannot be ascertained, however, is the relative position of the stimulation lead and the guiding tube, i.e. the rotational alignment of the stimulation lead within the guiding tube. This may be a negligible problem with unidirectional stimulation leads, but with directional stimulation leads becoming more and more customary for DBS, it is desirable to ascertain the spatial position of the stimulation lead including its distal portion with a plurality of directional electrodes at the target region.

The present invention provides a guiding tube that allows ascertain the spatial position (i.e. the spatial location and/or the spatial orientation) of a stimulation lead with respect to the guiding tube it is placed in. With the spatial position of the guiding tube known, it is eventually possible to determine the spatial position of each of the stimulation electrodes within the target region to be treated.

The guiding tube, the program and the placing system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

The guiding tube according to the present invention comprises a longitudinal, dimensionally stable tubular body encompassing an inner channel adapted to receive a stimulation lead, wherein at least one section of an otherwise electrically insulated inner surface of the tubular body has electroconductive properties.

In other words, the inventive guiding tube has a hollow tubular body that provides an inner channel for accommodating an elongated stimulation lead which may be formed to mate with the inner cross-sectional shape of the tubular body. Further the tubular body is dimensionally stable, i.e. it will maintain its form while being advanced through body tissue during a placement procedure for placing a stimulation lead accommodated within the tubular body. When the spatial position of a proximal portion of the guiding tube is known, the spatial position of a distal section of the guiding tube can be derived therefrom, as long as the overall shape of the guiding tube does deviate from its original shape. According to the present invention, the guiding tube body has at least one electroconductive section at its surface facing the inner channel, so that at least one electrode of a stimulation lead placed within the hollow guiding tube causes a short-circuit as soon as it contacts the electroconductive section. This short-circuit can be detected by a control unit assigned to the stimulation lead, for example by measuring the impedance on the electrodes of the lead. As the position of the electroconductive sections, the spatial position of the shorted electrodes can be determined, as well. This also applies to each electrode having a known position with respect to the shorted electrodes. With the geometrical arrangement of the electrodes provided on the lead known, it is then possible to determine the spatial position of each electrode with respect to the guiding tube and to the target region to be treated.

At least one of the electroconductive sections may have an open, non-circular cross-section in a plane perpendicular to the longitudinal axis of the tubular body. One can easily imagine that an electroconductive section extending over the entire circumference of the guiding tube (i.e. an electroconductive "ring") may help in determining the position of electrodes along the longitudinal axis of the guiding tube, but will deliver no information as to the rotational alignment of electrodes. In order to obtain information as to the angular position of the stimulation lead and its electrodes with respect to the guiding tube, an electroconductive section has to be provided, which, in a cross-sectional view of the guiding tube, covers only part of the inner surface of the guiding tube.

At least one electroconductive sections may further extend at least partially in a direction substantially parallel to the longitudinal axis of the tubular body. With an electroconductive section extending parallel to the longitudinal axis of the guiding tube, a plurality of electrodes can be shorted, which have a similar angular orientation on the stimulation lead. Moreover, at least one electroconductive section may have a longitudinal shape. Although the electroconductive sections may have any conceivable shape, a longitudinal shape, particularly a longitudinal shape that extends substantially parallel to the longitudinal axis of the guiding tube is more likely to short lead electrodes over a wide range within the guiding tube. In order to determine the spatial position of the guiding tube, even when the lead is advanced through the guiding tube, the guiding tube may further comprise at least one tracking marker coupled to the tubular body, wherein the at least one tracking marker is adapted to be identified by a medical tracking system. The tracking marker may be of any type that can be recognized by a corresponding medical tracking system, such as an optical tracking system, an EM tracking system or an ultrasound tracking system. Since the proximal portion of the guiding tube remains outside the body portion containing the target area, it may be beneficial to attach the tracking marker to the proximal portion of the guiding tube.

Further, at least one electroconductive section may be connected via an electroconductive interconnection to an interface for a sensor that is adapted to determine whether or not the corresponding section contacts at least one stimulation electrode, thereby causing a short-circuit. Such embodiment does not require to short at least two electrodes. Instead, it is just necessary to determine if one of the electrodes of the stimulation lead closes an electroconductive loop by contacting an electroconductive section provided at the inner surface of the guiding tube. On the other hand, a sensor is conceivable, which is adapted to determine a short-circuit between at least two electrodes contacting an electroconductive section of the guiding tube.

Further, the guiding tube may be adapted to be advanced through body tissue, particularly through brain tissue, which could be achieved by selecting a suitable material and shape for the guiding tube.

According to a further embodiment of the present invention, the inner surface of the guiding tube may have a rotationally asymmetric cross-section in at least one lengthwise portion. Such rotationally asymmetric inner surface of the guiding tube channel will prevent the stimulation lead from any rotational displacement of within the at least one lengthwise portion of the guiding tube, as long as the outer surface of the lead is correspondingly shaped to mate with the inner surface of the guiding tube. Thus, turning the guiding tube around its longitudinal axis will cause the lead to rotate by the same angle, as the lead is rotationally held by a form fit within the guiding tube. Nevertheless, the lead is freely movable along its longitudinal axis within the guiding tube.

With the stimulation lead being rotationally fixed within the guiding tube, determining the orientation of the stimulation electrodes within the guiding tube may not be necessary in case the initial rotational alignment of the stimulation lead within the guiding tube is known and remains unchanged while the stimulation lead is advanced to the target region. For that reason, the aspect of a rotationally asymmetric inner channel of the guiding tube may be considered as an independent invention, without the need of the guiding tube to have an above described electroconductive section for determining the relative position of the lead and the guiding tube. Such electroconductive section may however be employed to ascertain the longitudinal position of the lead within the guiding tube.

Moreover, the guiding tube may have a proximal interface section which is adapted to engage a correspondingly formed interface of a spatially fixed support structure, which provides a rotational interlock between the guiding tube and the spatially fixed support structure. For placing DBS leads, guiding tubes are held in a spatially fixed orientation with respect to the patient, but still have a translational degree of freedom along their longitudinal axis. Once the guiding tube is properly aligned, it can be advanced along a predetermined trajectory to a desired target region. If the guiding tube has an undesirable rotational orientation, it can be grasped at its proximal end and turned it about a certain angle. After the desired radial orientation of the lead has been reached, the proximal interface section of the guiding tube may then be locked to a corresponding interface that is held by a support structure such as a stereotactic arc. By doing so, the rotational alignment of the guiding tube the lead is maintained with the help of the support structure.

A further aspect of the present invention relates to a program and/or a program storage medium on which the program is stored, in particular in a non-transitory form, for placing a stimulation lead, wherein the program, when running on a computer, causes the computer to perform the method steps of:
  acquiring guiding tube position data describing the spatial position of the guiding tube described herein;
  acquiring contact data describing whether at least one directional electrode of the stimulation lead contacts at least one electroconductive section of the guiding tube;
  determining, based on said guiding tube position data and said contact data, electrode position data describing the spatial position of the at least one directional electrode.

According to the present invention, a computer may assist in placing a DBS-lead at a desired target region. At first, the computer may determine the spatial position of the guiding tube within three-dimensional medical space and relative to a target region the stimulation lead is to be placed in.

As soon as at least one electrode of the stimulation lead advanced through the guiding tube contacts an electroconductive section of the guiding tube, the position of the respective electrode can be calculated in the above described manner so that the spatial position of all of the stimulation lead electrodes is known. Eventually, this allows to verify a correct placement of a multi-directional stimulation lead within a target region.

A further aspect of the present invention relates to a stimulation lead placing system that comprises
  a guiding tube as described above;
  a computer on which the above described program is stored or run;
  a stimulation lead as described above, which is adapted to be inserted into the inner channel of the guiding tube and comprises at least one directional electrode;
wherein an outer diameter of the stimulation lead conforms to the inner diameter of the tubular body, enabling at least one electrode of the stimulation lead inserted into the inner channel to contact at least one electroconductive section.

The electroconductive section of the guiding tube may be adapted to short at least two directional electrodes of the stimulation lead. However, it is also conceivable that the electroconductive section is merely provided to close an electroconductive loop or circuit, which, as described above, allows to determine the spatial position of at least one electrode contacting the electroconductive section. On the other hand, the electroconductive section may be adapted to short at least two electrodes of the stimulation lead.

The stimulation lead placing system may further comprise a readout unit which is in particular connected to an interface of the guiding tube, the readout unit being adapted to determine whether at least one electrode of the stimulation lead contacts the at least one electroconductive section of the guiding tube. The read out unit may be part of a computer which is used to perform deep brain stimulation. However, the readout unit may be part of any other computer which is not integrated in the system adapted for deep brain stimulation.

As already referred to further above, the inventive stimulation lead placing system may employ a guiding tube and a stimulation lead with complementary rotationally asymmetric cross-sections in at least one lengthwise portion, so as to ensure a proper orientation of the stimulation lead electrodes within the target region. Such stimulation lead placing system may or may not employ a guiding tube that has an electroconductive section for determining the relative position of the lead and the guiding tube. The outer surface of the stimulation lead and the inner surface of the guiding tube may have a cross-sectional shape that allows the lead to be placed within the guiding tube in only one orientation. However, shapes are conceivable which allow the lead to be placed within the guiding tube in several, for example two or four distinctive orientations. For example, an oval shape would allow for two relative orientations of the lead within the guiding tube, wherein the lead has to be rotated by 180° between the possible orientations. On the other hand, a clover leaf shape allows for four different orientations of the lead within the guiding tube, wherein the lead has to be turned by 90° to reach the next possible orientation.

It is further conceivable that the stimulation lead protrudes from the distal end of the guiding tube when being placed in the guiding tube, particularly wherein at least one electrode placed at the distal end of the stimulation lead is not covered by the tubular body. With the electrodes being uncovered, DBS can be performed with the guiding tube not drawn out of the body tissue and still being placed around the stimulation lead, for example in a test-mode for verifying a proper placement of the lead.

The above described guiding tube, the above described program and the above described placing system may comprise any of the features disclosed in the following wherever technically expedient and feasible.

The guiding tube according to the present invention may have a tubular body comprising at least one electromagnetic element which is configured to exert an electromagnetic force on at least one magnetic element of a lead inserted into the inner channel.

The tubular body may further comprise at least one electromagnetic element to generate a directional electromagnetic field in the channel of the guiding tube. The electromagnetic element may be aligned in such a way that the electromagnetic field lines are oriented substantially perpendicular to the longitudinal axis of the tubular member. Generating an electromagnetic field passing through the channel of the tubular member will cause any magnetic element responsive to the electromagnetic field to align with the electromagnetic field lines, so that any lead inserted into the inner channel, that comprises a magnetic element can be aligned as desired within the channel. This may be done when the lead is inserted at a certain depth into the guiding tube, or even while the lead is inserted through the guiding tube, provided that an electromagnetic field is generated over a sufficient length of the channel. In that case, at least one electromagnetic element may extend over a substantial length of the tubular body, or even over the whole length of the tubular body, so that an electromagnetic field is generated over a sufficient length of the channel or even throughout the entire length of the channel.

A single electromagnetic element can provide two orientations for aligning a lead within the guiding tube, a first orientation with the inserted magnetic element oriented along the field lines, and a second, inverted orientation generated by an inverted polarity of the electromagnetic element causing an inverted orientation of the magnetic element. It is therefore conceivable that the tubular body comprises a plurality of electromagnetic elements disposed at different positions at the circumference of the guiding tube so as to provide a plurality of possible angular orientations for the lead within the guiding tube, depending on which of the electromagnetic elements is currently generating an electromagnetic field. It is generally conceivable that the guiding tube is advanced through body tissue with the lead already inserted into the inner channel and possibly even held in place with the help of the electromagnetic element. It is however also conceivable to advance the guiding tube through tissue towards the target region first, so that the lead can be introduced into the channel afterwards.

The tubular body may be adapted to receive a stimulation lead, particularly a stimulation lead for DBS, which may comprise at least one directional electrode. The guiding tube may further be adapted to be advanced through body tissue, particularly through brain tissue, which could be achieved by selecting a suitable material and shape for the guiding tube.

The spatial position of the electromagnetic guiding tube may be determined by means of an EM tracking system. The guiding tube may further comprise at least one tracking marker which is coupled to the tubular body, and which is adapted to be identified by a medical tracking system, particularly a non-optical IGS tracking system, specifically an EM tracking system. With the help of the medical tracking system identifying the spatial position (i.e. the spatial location and/or orientation), the overall spatial position of the guiding tube can be calculated so that the correct position of the guiding tube with respect to the target region can be ascertained. In order to obtain a desired orientation of the electrodes provided at the distal portion of the stimulation lead, an electromagnetic element is switched on to generate an electromagnetic field, which will cause the magnetic element of the lead within the guiding tube to align along the field lines. As the magnetic element is fixedly held by the stimulation lead, applying the electromagnetic field will also cause the stimulation lead to orient in a direction that is defined by the electromagnetic field. As the orientation of the electromagnetic field is known or at least determinable, for example via the medical tracking system, the electrodes of the stimulation lead can be brought into a desired orientation with respect to the target region to be treated. Further, it is conceivable to carry out corrections on the orientation of the electrodes with respect to the target region by simply rotating the guiding tube around its central longitudinal axis, since this will also rotate the stimulation lead as long as the electromagnetic field is applied.

The at least one electromagnetic element of the guiding tube may be provided at a distal portion of the guiding tube, particularly at a portion adjoining at least one directional electrode of a stimulation lead inserted into the inner channel. Medical implants such as DBS-leads or infusion cannulae usually have the "functional portion" at their distal end, which is the reason why it is the distal end that has to be properly oriented. It therefore might be sufficient to provide an electromagnetic element for the distal portion of the guiding tube only, which is adjacent to the distal portion of the lead when the lead is fully introduced into the inner channel of the tubular body. After the lead has been fully introduced into the inner channel of the guiding tube, the electromagnetic element can be switched on to properly align the distal portion of the lead. On the other hand, an electromagnetic element may extend in a longitudinal direction over a larger portion of the guiding tube, even over substantially the whole extension of the guiding tube. By doing so, an electromagnetic field can be applied while the lead is advanced through the said guiding tube, such that the lead is aligned in a desired orientation even before it reaches its final position within the guiding tube.

It is further conceivable that at least one electromagnetic element has a shape that, viewed in a plane perpendicular to the longitudinal axis of the tubular body, at least partially runs around the circumference of the tubular body. Up to a certain limit, the electromagnetic force applied on a magnetic element within the channel increases with the cross-sectional area of the tubular member, covered with the electromagnetic element. However, an electromagnetic element running around the circumference of the tubular body over more than 180° is counterproductive as the resulting electromagnetic force will decrease again. It was found that an electromagnetic element covering approximately one third of the overall circumference of the tubular body provides desirable results.

The stimulation lead may have an elongated body portion that is adapted to be inserted into an inner channel encompassed by a tubular body of a guiding tube, wherein at least one magnetic element is provided on or in the body portion. The body portion of the lead may be flexible, since the guiding tube provides sufficient support against unintended bending while the lead is advanced to the target region within the guiding tube or together with the guiding tube. As already mentioned above, the lead may have at least one magnetic element which is responsive to an electromagnetic field generated by an electromagnetic element of a corresponding guiding tube.

At least one magnetic element may be provided at a distal portion of the lead in a region where the "functional portion" of the lead is provided, as well. This ensures that the functional portion of the lead in particular is aligned as desired.

It is conceivable that the magnetic element of the lead is an electromagnet which can be switched on and switched off. With a guiding tube having already an electromagnet for generating an electromagnetic field, it is conceivable to provide in or on the lead a permanent magnet having ferromagnetic properties, which is fixedly held in or on the instrument such that the instrument is aligned within the guiding tube as soon as an electromagnetic field is applied on the lead.

The program may cause the computer to perform the method steps of:
  acquiring guiding tube position data describing the spatial position of the guiding tube described herein;
  acquiring relative position data describing the position of the stimulation lead, particularly the position of at least one directional electrode relative to the guiding tube;
  determining, based on the guiding tube position data and the relative position data, absolute position data describing the absolute spatial position of the stimulation lead, particularly the absolute spatial position of at least one directional electrode.

The guiding tube position data can be acquired with the help of any suitable tracking system which is able to identify a medical tracking marker coupled to the guiding tube, allowing the spatial position of the guiding tube to be calculated. As soon as the electromagnetic element of the guiding tube is switched on so as to generate an electromagnetic field, the lead will align in a predefined way within the guiding tube. Since the orientation of the electromagnetic field is known with respect to the guiding tube, the orientation of the aligned lead within the guiding tube is also known and can be calculated by means of a medical navigation system. Based on this data, the absolute position (location and/or alignment) of the lead and its functional portion can be calculated and it can be valuated whether or not the lead and its functional portion is placed as desired within a target region, the position of which is also known to the medical navigation system.

The placing system may further comprise:
  the guiding tube and the stimulation lead described above;
  a computer on which the above described program is stored and/or run; and
  a control unit connected to the at least one electromagnetic element, and adapted to cause the electromagnetic element to exert an electromagnetic force on the magnetic element of the stimulation lead which is inserted into the inner channel of the guiding tube.

The control unit may be integrated in a computer assigned to a medical navigation system, or may be provided as a separate unit for controlling the stimulation lead placing system. Moreover, the control unit may be a simple control element such as a switch, which allows medical personnel to manually switch on and off the at least one electromagnet for aligning the lead within the guiding tube. However, it also conceivable that the lead is aligned within the guiding tube automatically. For example, the medical navigation system may automatically switch on an electromagnet as soon as it recognizes that the guiding tube is about to be placed within the patient.

DEFINITIONS

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the World Wide Web (WWW) and located in a so-called cloud of computers which are all connected to the World Wide Web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet.

The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a tracking marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

BRIEF DESCRIPTION OF DRAWINGS

In the following, the invention is described with reference to the enclosed Figures which represent preferred embodiments of the invention. The scope of the invention is not however limited to the specific features disclosed in the Figures, which show.

DETAILED DESCRIPTION

Figure 1:
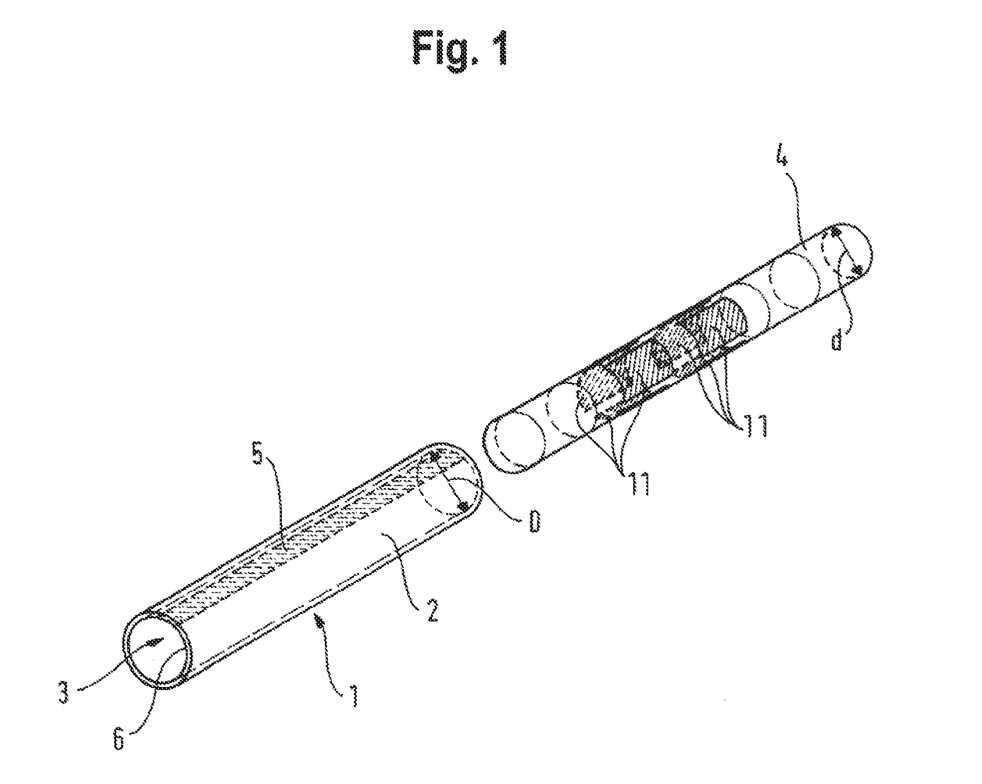
FIG. 1 a first embodiment of a guiding tube and a corresponding stimulation lead.

FIG. 1 shows a first embodiment of the inventive guiding tube 1 which comprises a tubular body 2 and an electroconductive section 5 provided at the inner surface 6 of the tubular body 2. The body 2 encompasses a circular channel 3 having an inner diameter D, into which a stimulation lead 4 can be placed. The stimulation lead 4 has a circular cross-sectional shape having an outer diameter d that corresponds to the shape of the channel 3 of the guiding tube. This ensures that the electrodes 11 provided at the outer surface of the stimulation lead 4 contact the electroconductive section 5 as soon as the electrodes 11 reach the electroconductive section 5 which is provided at the inner surface 6. Apart from section 5, the inner surface 6 of the tubular body 2 is non-conductive. It becomes apparent from FIG. 1 that the longitudinal section 5 extending parallel to the longitudinal axis of the tubular body 2 is about to short electrodes 11 which are arranged in a longitudinal direction of the stimulation lead 4.

Figure 2:
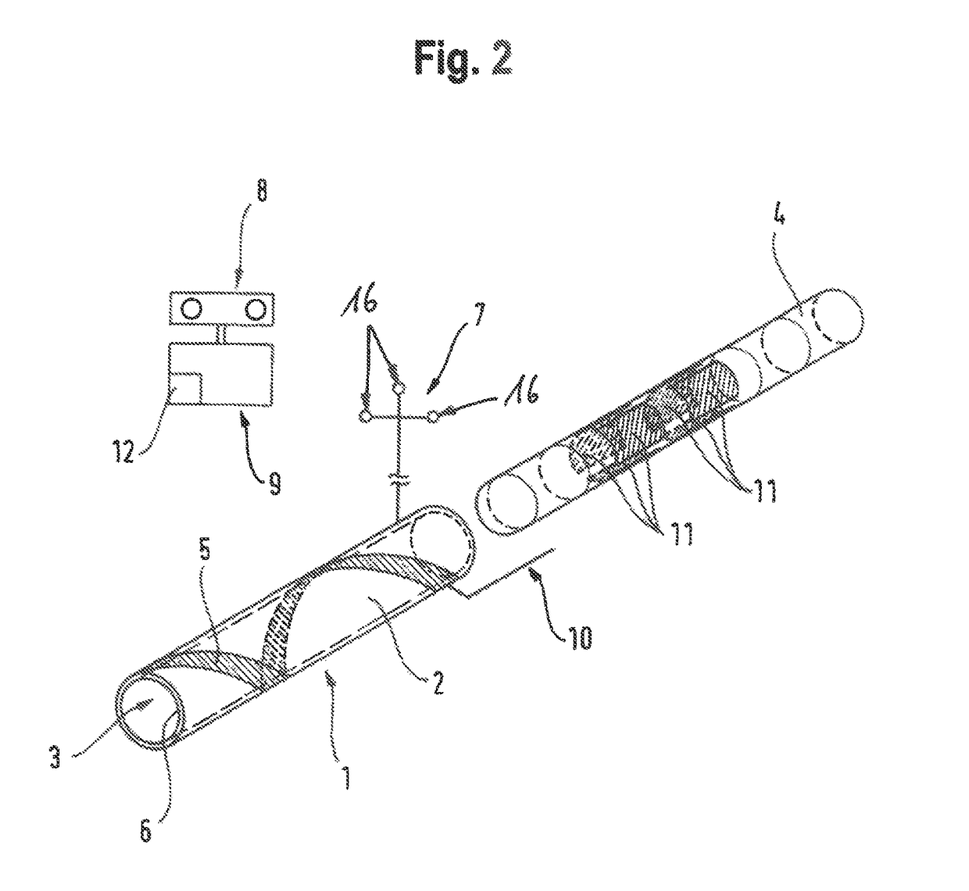
FIG. 2 a second embodiment of a guiding tube and a corresponding stimulation lead.

FIG. 2 shows a guiding tube 1 which mostly resembles the guiding tube shown in FIG. 1, but comprises an electroconductive section 5 which has a spiral shape. Further, the electroconductive section 5 is connected to an interface 10, so that an electroconductive circuit including the lead supply lines for the electrodes 11, electrode 11, section 5 and interface 10 is closed as soon as at least one of the electrodes 11 contacts section 5.

An impedance measurement on the electrodes 11 immediately indicates when at least one of the electrodes 11 of the lead 4 shown in FIG. 2 or at least two of the electrodes 11 of the lead 4 shown in FIG. 1 contact section 5, so that the position of the stimulation lead 4 and therefore also the position of the electrodes 11 can be calculated with respect to the guiding tube 1. Since the spatial position of the guiding tube 1 is determined with the help of the camera array 8 of a medical navigation system detecting the marker array 7 with three tracking markers 16 attached to the proximate end of the guiding tube 2 and detected by, the spatial position of the stimulation lead 4 and of each of the electrodes 11 can be calculated.

Figure 3:
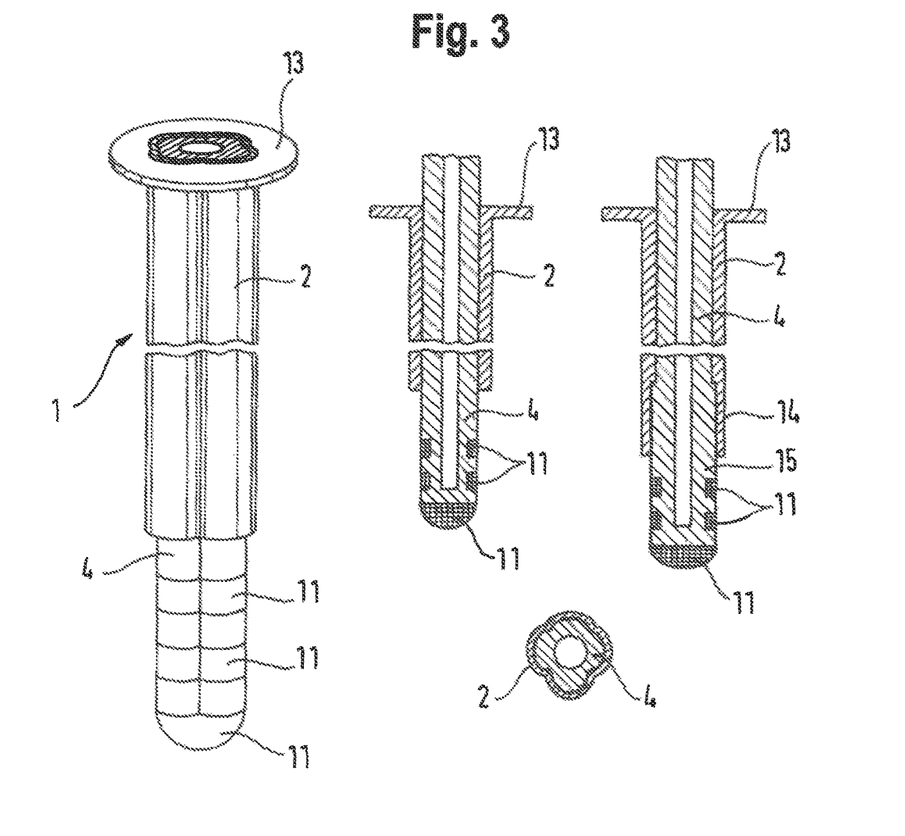
FIG. 3 a third embodiment of a guiding tube and a corresponding stimulation lead.

FIG. 3 shows a further embodiment of the inventive guiding tube 1. The inner channel 3 of the guiding tube has an asymmetric cross-sectional shape with four bulges, three of the bulges being identical, wherein the fourth bulge has a different shape. This will allow the stimulation lead 4 to be placed within the guiding tube 1 with one specific orientation only. The guiding tube 1 further comprises a disk-shaped interface section 13 provided at its proximal end, which can be grasped by a person so as to rotate the guiding tube 1 around the central longitudinal axis of the guiding tube 1. The form fit provided by the mating asymmetric cross-sectional shapes of channel 3 and the stimulation lead 4 rotationally holds the stimulation lead 4 in place while the guiding tube 2 is being turned. For holding the stimulation lead 4 in place, it is not even necessary for the inner channel 3 or the stimulation lead 4 to have an asymmetric cross-sectional shape over their entire length, as this is shown in the left cross-sectional view shown in FIG. 34. As shown in the right cross-sectional view in FIG. 3, it is rather sufficient to provide at least one lengthwise portion 14, preferably at the distal end of the guiding tube 1, and a corresponding lengthwise portion 15, preferably at the distal end of the stimulation lead 4, for holding the stimulation lead 4 in place.

FIG. 3 further shows that the stimulation lead 4 together with the electrodes 11 protrudes from the distal end of the tubular body 2 when being placed within the guiding tube 1.

Figure 4:
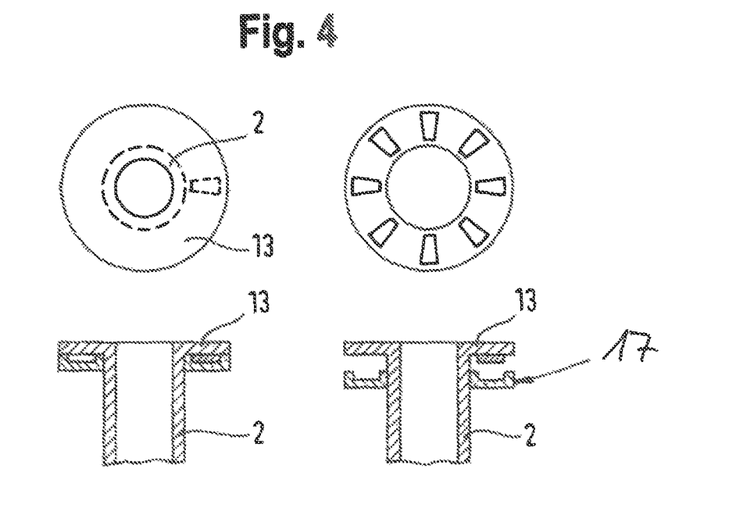
FIG. 4 a detailed view on the proximal end of the guiding tube shown in FIG. 3.

FIG. 4 shows in detail the proximal end of the guiding tube 1 together with a corresponding interface assigned to a support structure 17 such as a stereotactic arc. At the proximal end of the guiding tube 1, a disc-shaped interface section 13 is integrally formed with the tubular body 2, which comprises at its downward facing side a ridge. A corresponding disc that may be rigidly attached to a stereotactic arc has one central hole the tubular body 2 is placed through, and several receptacles arranged at the disc's circumference, which are to receive the ridge of disc 13.

As long as disc 13 is spaced from the corresponding disc attached to the support structure 17 (as shown in the lower right depiction in FIG. 4) the guiding tube can be rotated with respect to the stereotactic arc. As soon as a desired rotational orientation of the guiding tube has been reached, the rotational alignment of the guiding tube is fixed by snap-fitting disc 13 onto the corresponding disc of the stereotactic arc by pushing the tubular body 2 through the corresponding opening of the disc of the stereotactic arc so that the ridge engages one of the receptacles, thereby maintaining the rotational orientation of the guiding tube 1 and the stimulation lead 4 placed therein.

The invention claimed is:

1. A guiding tube for stimulation leads, comprising:
   a longitudinal, stiff tubular body encompassing an inner channel adapted to receive a stimulation lead;
   wherein at least one section of an otherwise electrically insulated inner surface of the stiff tubular body has electroconductive properties, and wherein the at least one section has an open, non-circular cross section in a plane perpendicular to the longitudinal axis of the tubular body.

2. The guiding tube according to claim 1, wherein at least one section extends at least partially in a direction substantially parallel to the longitudinal axis of the tubular body.

3. The guiding tube according to claim 1, wherein at least one section has a longitudinal shape.

4. The guiding tube according to claim 1, further comprising at least one tracking marker coupled to the tubular body, the at least one tracking marker being adapted to be identified by a medical tracking system.

5. The guiding tube according to claim 1, further comprising an interface having an electroconductive interconnection to the at least one electroconductive section.

6. The guiding tube according to claim 1, wherein the guiding tube is adapted to be advanced through body tissue.

7. The guiding tube according to claim 1, wherein the guiding tube has in at least one lengthwise portion a rotationally asymmetric cross-section.

8. The guiding tube according to claim 1, wherein the guiding tube has a proximal interface section adapted to engage a correspondingly formed interface of a spatially fixed support structure, thereby providing an interlock between the guiding tube and the spatially fixed support structure.

* * * * *